(12) United States Patent
Berger et al.

(10) Patent No.: US 6,916,608 B2
(45) Date of Patent: Jul. 12, 2005

(54) COMPOSITION FOR PROVIDING LONG TERM STABILITY TO CELLS FOR DIAGNOSTIC TESTING

(75) Inventors: Dolores M. Berger, Baltimore, MD (US); Daretta A. Yursis, Parkton, MD (US); William A. Nussbaumer, Timonium, MD (US); Anne B. Brown, Seaford, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/394,006

(22) Filed: Sep. 10, 1999

(65) Prior Publication Data

US 2002/0009722 A1 Jan. 24, 2002

(51) Int. Cl.[7] ............................. C12Q 1/68; G01N 1/30
(52) U.S. Cl. ............................. 435/6; 435/7.1; 435/7.2; 435/7.21; 435/7.3; 435/40.5; 435/40.52
(58) Field of Search .............................. 435/6, 7.1, 7.2, 435/7.21, 7.32, 40.5, 40.52

(56) References Cited

U.S. PATENT DOCUMENTS

| | | | |
|---|---|---|---|
| 3,852,155 A | | 12/1974 | Moore |
| 5,229,265 A | * | 7/1993 | Tometsko ...................... 435/6 |
| 5,232,688 A | | 8/1993 | Ziegler et al. |
| 5,422,277 A | * | 6/1995 | Connelley et al. ............ 436/10 |
| 5,514,367 A | | 5/1996 | Lentini et al. |
| 5,521,061 A | * | 5/1996 | Bresser et al. ................. 435/5 |
| 6,162,931 A | * | 12/2000 | Gee et al. .................... 549/223 |
| 6,207,408 B1 | * | 3/2001 | Essenfeld et al. |
| 6,232,092 B1 | * | 5/2001 | Rogers |

FOREIGN PATENT DOCUMENTS

| | | |
|---|---|---|
| EP | 0 576 188 A1 | 6/1993 |
| EP | 0 772 972 B1 | 10/2002 |
| WO | WO-90/02204 A1 * | 3/1990 |

OTHER PUBLICATIONS

Baltzer et al "Solvent Effects on the Recemization of Optically Active Biphenyl Derivatives" Acat Chemica Scandinavica, 1982, 36: 31–38.*
Academic Press Dictionary of Science and Technology, Academic Press, 1992, p. 837.
Dent et al. "A whole–mount immunocytochemical analysis of the expression of the intermediate filament protein vimentin in Xenopus" Development, 1989, 105: 61–74.*
Williams et al. "Ethanol Fixation of Sputum Sediments for DNA–Based Detection of Mycobacterium Tuberculosis" Journal of Clinical Microbiology, 1995, 33(6): 1558–1561.*
Leif et al., J. of Histochem. and Cytochem., 1977; 25(7):525–534.
Otto, et al., Analyt. and Quant. Cytol., 1979; 1:127–135.
VanDriel–Kulker et al., Analyt. and Quant. Cytol., 1980; 2:243–246.
Oud et al., Analyt. and Quant. Cytol., 1981; 6:73–80.

* cited by examiner

Primary Examiner—B J Forman
(74) Attorney, Agent, or Firm—Allan M. Kiang (57) ABSTRACT

The present invention relates to a method and composition for stabilizing clinical specimens (i.e., cells in biological samples) for transport and subsequent testing for diagnosis. The composition is specifically capable of maintaining nucleic acid in the cells intact for hybridization with oligonucleotide capture and detector probes.

11 Claims, 6 Drawing Sheets

COMPOSITION FOR PROVIDING LONG TERM STABILITY TO CELLS FOR DIAGNOSTIC TESTING

FIELD OF THE INVENTION

The present invention relates to a method and composition for stabilizing cells in a sample (such as, for example, a clinical specimen in a biological sample) for transport and subsequent testing for diagnosis. The composition for stabilizing the cells is specifically capable of maintaining nucleic acids intact for hybridization with oligonucleotide capture and detector probes.

BACKGROUND OF THE INVENTION

Diagnostic testing of infectious and sexually transmitted diseases has become increasingly focused on faster, more accurate results. Nucleic acid probe technology has enabled rapid diagnostic testing to break time-to-result barriers with high specificity, and less subjectivity. While they are faster than growth based, biochemical assays, and more specific than immunologically based assays, nucleic acid probe assays present a unique challenge for delivering the target sample intact. Furthermore, samples that may be collected at one site, and tested at another site, are particularly vulnerable to nucleic acid degradation if not handled properly.

Nucleic acid detection by hybridization and capture has been applied to a host of diseases. It has been especially useful for infectious diseases in which conventional methods are time consuming, expediency of treatment is critical, and/or the disease is reportable to health agencies. *Trichomonas vaginalis* vaginitis (trichomoniasis) is a reportable sexually transmitted disease that affects approximately 3 million women per year in the U.S. Furthermore, vaginal disorders due to bacterial vaginosis (BV) and candidiasis, are two of the most common reasons women seek medical treatment. The symptoms of these three distinct diseases overlap, thus creating a need for differential diagnosis before appropriate and specific medication can be prescribed. A rapid and accurate diagnosis is especially critical in pregnant women, in whom BV and trichomoniasis are associated with premature births and low birth weight babies. Moreover, BV-positive pregnant women are predisposed to chorioamnionitis, amniotic fluid infection, and puerperal infectious morbidity. BV has also been associated with pelvic inflammatory disease, postpartum endometritis, bacteremia, salpingitis, and the like. Proper diagnosis and treatment of vaginitis requires identifying the causative microorganism so that the appropriate antimicrobial treatment can be defined.

The Affirm VPIII nucleic acid hybridization assay, described in U.S. Pat. No. 5,654,418, is a significant advance in the diagnosis of vaginitis, due to its ability to detect *T vaginalis, G. vaginalis* or *C. albicans*, from a single vaginal swab. The swab is incubated in a lysis solution at high temperature, which causes the organism to lyse and release nucleic acid. A buffer solution is then added to the sample. The sample solution is next incubated with a set of nylon beads that are each derivatized with specific capture probes. The rRNA hybridizes to the capture beads, which are next incubated with a solution containing biotinylated detector oligonucleotide probes. The detector probes hybridize to another region in the rRNA. The bead is transferred to a well containing an enzyme. If biotinylated detector probes are hybridized to the rRNA, the enzyme will bind to the biotin. If there is no rRNA hybridized to the bead, no biotinylated detector probe will be present for the enzyme to bind. Finally, the beads are incubated with a substrate, which will react with the enzyme to form a blue color. If rRNA is present the beads will appear blue. If there is no rRNA in the sample, the beads remain colorless. A differential diagnosis can be obtained from a single sample by using three beads, each bead specific for only one of the analytes.

The present invention was developed to provide stability to vaginal swab samples, specifically, samples collected to test for the presence of Candida, Gardnerella or Trichomonas, using the Affirm VPIII Microbial Identification Test. Without the aid of the present invention, the swab samples will only remain stable for up to one hour at ambient temperature, or four hours at refrigerated temperature. Specifically, the rRNA within the cells must remain intact in order to be detected, and, the presence of low, non-pathological numbers of Candida must be kept from multiplying and producing a false positive. The proper preservative would allow for sample collection and sample testing to be conducted at remote sites, or for numbers of samples to be batched for processing and testing all at once.

The appropriate transport or preservative or fixative solution for the Affirm VPIII sample needed to have the following attributes:

1. The solution had to control or inhibit RNA degrading enzymes (RNases) found in vaginal fluid.
2. It had to prevent growth of Candida, Gardnerella or Trichomonas, while . . .
3. controlling RNA degradation within the cells due to endogenous nucleases or cell death.
4. The solution had to be compatible with the Affirm VPIII test as embodied.
5. It could not introduce unnecessary risk to the end users, and
6. It would provide signal stability for samples stored up to 72 hours.

Conventional preservatives, such as those having bactericidal or inhibitory effects, prevent growth of low levels of organisms, but do not address the problem of nucleic acid degradation. Conversely, transport media tend to be minimal or starvation media, formulated to maintain viability of the organism for culture later. Candida, however, tend to flourish in such media, while Gardnerella and Trichomonas do not survive. The result with such media is a false positive Affirm result for Candida and a false negative for the latter two. The complexity of the problem is increased by the fact that these three organisms represent both prokaryotic and eukaryotic cell types, and each has a distinctly constructed cell wall and/or membrane.

Fixatives, as a class of substances, tend to contain alcohol, formaldehyde or chloroform, and a wide range of additives, depending on the specimen and application. Many are not stable solutions, suitable only for use within hours of preparation. Furthermore, they may present hazards beyond those already faced by the clinician (i.e., mercuric chloride, picric acid). Formaldehydes were found to be incompatible with Affirm reagents. Alcohol based fixing agents offered the most promise due to their ability to precipitate or denature proteins, particularly, nucleases.

One such fixative is described in U.S. Pat. No. 5,256,571, for preserving the structure of mammalian cells. Hurley et al claim a solution (designated from here on as PreservCyt) of 45 to 55% methanol, an anti-clumping agent and a buffering agent. However effective this solution may be for mammalian cells, it was not capable of meeting the criteria outlined above for all three vaginal pathogens of interest. This was most likely due to the added complexity of the cell wall structure of each organism, a structure not encountered in mammalian cells. Furthermore, in these studies, increasing the methanol concentration to 95% did not preserve, or fix, the vaginal samples such that the rRNA was detectable after 24 hours.

Many fixatives used for cytology and histology are home-brewed solutions, the formulations of which are well known to those skilled in the art. They are frequently prepared fresh and used within a short period of time, as mentioned above. Such solutions may include for example: 10% neutral buffered formalin, Carnoy's solution (ethanol, chloroform, acetic acid), B-5 (mercuric chloride, sodium acetate, formalin, water), Bouin's solution (picric acid, glacial acetic acid, formaldehyde), and Zenker's solution (water, potassium dichromate, mercuric chloride, glacial acetic acid). These formulations are routinely published in reference pages, via the internet, by academic or research institutions such as: the University of Bristol's Department of Pathology & Microbiology (lang-dl-srv.lang.bris.ac.uk/Cpl/histfix.htm), The Jackson Laboratory (jax.org/resources/documents/sss/imaging/histf.html), and the University of Newcastle at Australia (newcastle.edu.au/department/bi/birjt/techinfo/bio__fix.html). One lesser known fixative, published via the internet by the University of Texas, Austin (vize222.zo.utexas.edu/Marker__pages/methods__pages/fixatives.html), is known as Dents solution. This solution contains four parts methanol and one part dimethyl sulfoxide (DMSO). Dents solution is described as a fixative used for immunological staining of Xenopus specimens. The specified protocol is to fix samples at −20° C. overnight. The authors claim that samples prepared in this manner may be stable frozen for many months, perhaps years.

It has been found by the inventors that the above described Dents solution will preserve vaginal swab samples containing vaginal fluid and seeded quantities of *Trichomonas vaginalis, Gardnerella vaginalis*, and *Candida albicans*. Swabs stored in this solution are stable for several days at ambient temperature, prior to testing in the Affirm VPIII system. Results obtained with such swabs give similar signals to identical swabs tested immediately after preparation. It has also been found by the inventors that ethanol, or mixtures of ethanol and methanol, will also preserve the samples when mixed with DMSO. The preferred embodiment uses a 1:1 mix of methanol and DMSO.

Dimethyl sulfoxide has been used as an ingredient mixed with other molecules in previous references but in significantly smaller concentrations. U.S. Pat. No. 5,622,867 uses 0.5 to 6% DMSO in a solution to store blood platelets; U.S. Pat. No. 3,852,155 uses 8 to 10% DMSO in a solution for cryopreserving equine cell cultures; U.S. Pat. No. 5,364,756 describes a solution containing 0.5M (~3–4%) DMSO. U.S. Pat. Nos. 5,422,277 and 4,666,699 use DMSO in stain-fixative solutions at 5 to 10% and 3 to 8% respectively. However, in every one of these instances, DMSO is only a small fractional component of a much more complex solution.

In the present invention, the inventors describe a novel composition which is a mixture of a first substance which is at least one alcohol or ketone and a second facilitating substance such as DMSO, with a preferred embodiment being a mixture of 50% methanol/50% DMSO, and the method of providing long term (several days) stability, for example, to cells and in particular, clinical specimens, utilizing this composition.

Specifically, in a preferred embodiment, the clinical specimens are considered to be vaginal swabs, containing the causative agents for vaginitis and bacterial vaginosis, however, the solution could be used for other biological specimens in which the recovery of RNA is necessary. This solution will be useful in preventing the degradation of nucleic acids (i.e., DNA, RNA) located within cells, suspended in a matrix of biological fluid such as vaginal fluid. Furthermore, this solution will be capable of preventing degradation of, for example, RNA, an easily degraded nucleic acid, over several days at ambient temperatures and above.

SUMMARY OF THE INVENTION

The present invention provides a novel cellular fixative composition and method of cell (and further, clinical specimen) preservation.

In a preferred embodiment, the composition of the present invention is comprised of a first substance capable of precipitating or denaturing proteins; and a second facilitator substance to aid in the infusion of the first substance into cells.

In one embodiment of the present invention the composition is comprised of 4 parts methanol to 1 part DMSO.

In another embodiment of the present invention the composition is comprised of 2.5 parts methanol, 2.5 parts ethanol, and 5 parts DMSO.

In yet another embodiment of the present invention the composition is comprised of 4 parts ethanol and 1 part DMSO.

In a preferred embodiment of the present invention, the composition is comprised of 1 part methanol and 1 part DMSO.

In another embodiment of the present invention, the composition is comprised of a single substance which can perform both functions of precipitating or denaturing proteins, and aiding in the infusion of the substance into cells.

In a preferred embodiment of the present invention, the composition is comprised of methanol only.

In another preferred embodiment of the present invention, the composition is comprised of dimethyl sulfoxide only.

BRIEF DESCRIPTION OF THE DRAWING

FIG. 1 (A–E) is a schematic description of the Affirm VPIII nucleic acid hybridization assay.

DETAILED DESCRIPTION OF THE INVENTION

The present invention provides a novel fixative composition and method for preserving cells in a sample, preferably a biological sample.

The composition of the present invention is comprised of:
I. a first substance capable of precipitating or denaturing proteins, comprised of at least one alcohol or ketone; and
II. a second facilitator substance to aid in the infusion of the first substance into cells.

The alcohol or ketone may be one or more of the following: methanol, ethanol, propanol, isopropanol, butanol or acetone. The facilitator substance can be dimethyl sulfoxide, ethylene glycol, polyethylene glycol, or others familiar to those skilled in the art.

There are several preferred embodiments of the composition of the present invention The composition can be comprised of methanol:DMSO in a 4:1 ratio; methanol:ethanol:DMSO in a 2.5:2.5:5.0 ratio,; ethanol:DMSO in a 4:1 ratio; or most preferably, methanol:DMSO in a 1:1 ratio. Other preferred embodiments include where the composition is comprised of methanol only or dimethyl sulfoxide only.

In one preferred embodiment, the method of the present invention is directed to stabilizing the structure and nucleic acids of at least one cell in a sample, wherein said method comprises:
(a) adding to a vessel containing the sample, a composition comprising an effective concentration of a substance capable of precipitating or denaturing proteins and capable of aiding in the infusion of said compound into said at least one cell;
(b) contacting said at least one cell in said sample with said composition;
(c) incubating said sample with said composition for an effective period of time and at an effective temperature; and
(d) obtaining said at least one cell with stabilized structure and nucleic acids in said sample.

The substance can be methanol, ethanol, propanol, isopropanol, butanol, acetone, dimethyl sulfoxide, ethylene glycol and polyethylene glycol.

In another preferred embodiment, the present invention relates to a method for stabilizing the structure and nucleic acids of at least one cell in a sample, wherein said method comprises:
(a) adding to a vessel containing the sample, a composition comprising an effective concentration of:
  (i) a first substance capable of precipitating or denaturing proteins, comprising at least one alcohol or ketone; and
  (ii) a second facilitator substance to aid in the infusion of the first compound into the at least one cell;
(b) contacting said at least one cell in said sample with said composition;
(c) incubating said sample with said composition for an effective period of time and at an effective temperature; and
(d) obtaining said at least one cell with stabilized structure and nucleic acids in said sample.

The alcohol or ketone may be one or more of the following: methanol, ethanol, propanol, isopropanol, butanol or acetone. The facilitator substance can be dimethyl sulfoxide, ethylene glycol, polyethylene glycol or others familiar to those skilled in the art.

Specifically, vaginal swab samples fixed with the invention are stable for up to four days at ambient temperature and above, when stability is assessed as detectable Trichomonas, Gardnerella or Candida ribosomal RNA.

In a preferred embodiment, the invention can be used with the Affirm VPIII nucleic acid hybridization assay, described in U.S. Pat. No. 5,654,418. However, the present invention is also intended for use with other test methods that rely on the integrity of nucleic acid for diagnosis.

Since the present invention preserves nucleic acid, and in a particularly preferred embodiment, RNA, in a prokaryotic cell type including, but not limited to, *Gardnerella vaginalis* (a Gram-negative bacterium) and a eukaryotic cell type, including but not limited to *Candida albicans* (a yeast) and *Trichomonas vaginalis* (a protozoan), it would be obvious to those skilled in the art that the preserving effects of the present solution can be applied to any other prokaryotic and eukaryotic cells, and is intended to be applicable to any other prokaryotic and eukoryotic cells.

Figure 1:
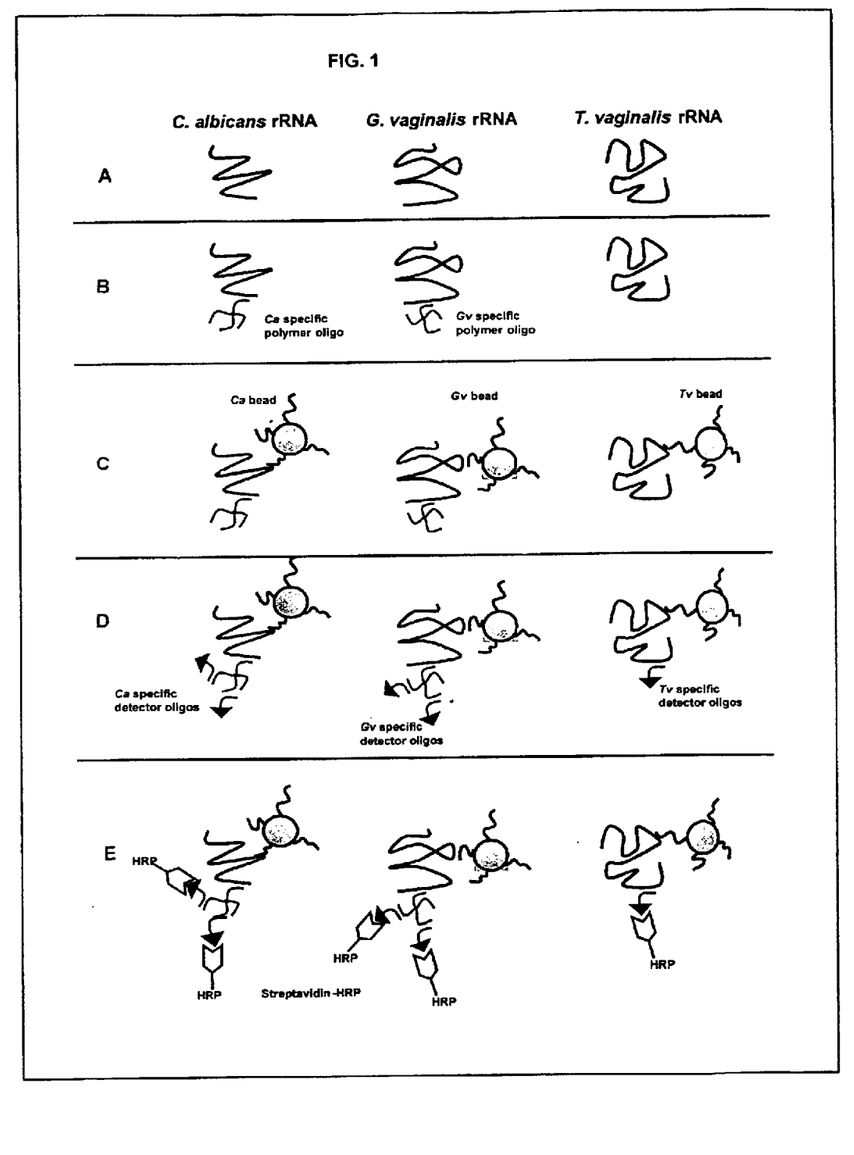

In the preferred embodiment, vaginal swabs are placed in the Affirm VPIII tube, and a volume of the novel fixative (50 to 500 uls, preferably 100 uls), is added to the tube. Sample tubes are capped, and the samples can then be transported at ambient temperature to the site of testing. Testing can take place up to four days later. When ready for testing, a lysis solution is added to the tube, and the tube is capped and incubated at 85° C., which causes the organism to lyse and release nucleic acid (FIG. 1A). After lysis and cooling, a buffer solution containing oligonucleotide probe polymers specific for 16s ribosomal ribonucleic acid (rRNA) of *G. vaginalis* and *C. albicans* is then added, forming a complex (FIG. 1B). The polymer is not required for *T vaginalis* because of the higher copy number of rRNA transcripts. The complex is then removed from the sample by a capture oligonucleotide that hybridizes to another site on the rRNA. There are three different capture oligonucleotides, each having unique specificity for *T. vaginalis*, *G. vaginalis* or *C. albicans*. Nylon beads are derivatized with only one type of capture oligonucleotide. One bead of each type is incubated with the sample, allowing for the simultaneous capture of rRNA of three distinct organisms (FIG. 1C). The beads are next incubated in a solution containing biotinylated detector oligonucleotide probes. The detector probes hybridize to another region in the rRNA (FIG. 1D). After washing, the bead is transferred to a well containing streptavidin conjugated to horseradish peroxidase (SA-HRP). If biotinylated detector probes are hybridized to the rRNA, the SA-HRP will bind to the biotin (FIG. 1E). If there is no rRNA hybridized to the bead, no biotinylated detector probe will be present for the SA-HRP to bind. Finally the beads are incubated with a substrate which will react with the HRP to form a blue color. If rRNA is present the beads will appear blue; if it is not present the beads remain colorless.

Alternative detection reagents can be used for research purposes to provide a quantitative measure of the relative amount of rRNA hybridized to the bead. After binding SA-HRP, beads can be incubated with a chemiluminescent HRP substrate in microtitre wells, and read in a luminometer.

In order to be effective, the fixative solution needs to inhibit or shut down the nucleases that are present in vaginal fluid matrix. Secondly, it has to permeate the organism and prevent nucleic acid degradation due to endogenous nucleases. Thirdly, it must leave the organism cell wall intact. Premature lysis of the organisms can result in a loss of some RNA when the sample is heated with the lysis solution in the Affirm VPIII assay. Fourthly, the fixative solution must be compatible with the Affirm VPIII reagents, not producing any artifact.

Many fixatives used for tissue fixation, staining and cryopreservation are complex solutions, often containing harsh reagents, with very limited stability. This is often necessary when the preservation of cellular structures or proteins is critical. Because the intent here is to preserve only the nucleic acid and cell wall, it is considered that the solution can be much less complex. An added benefit of the reduced complexity is a more stable solution.

Here it is described that mixtures of alcohol(s) and DMSO or these compounds alone are capable of stabilizing specimens, specifically vaginal swabs inoculated with causative agents for vaginitis and bacterial vaginosis. The novel solutions can serve as transport media for clinical specimens, which may be collected at remote sites and tested later at a centrally located processing laboratory. No special transport considerations are necessary, beyond careful handling and avoidance of temperature extremes.

The following are specific examples of the present invention, but should not in any way be considered limitations thereof.

EXAMPLE 1

Description of the Affirm VPIII Microbial Identification Test

A description of the Affirm VPIII Microbial Identification Test and the Test protocol are as follows:

Collected vaginal swab samples are placed in the Affirm VPIII sample tube, and the swab shaft is snapped off at the score (just above the top of the tube). Twelve drops of Lysis Solution are added to each tube (with swabs remaining in the tubes), and the tubes are capped and placed in the Affirm Lysis block (at 85° C.) for ten minutes. The tube caps "capture" the swab shaft to facilitate later removal of the swab. After ten minutes, the tubes are removed from the block, and twelve drops of Buffer solution are added to each tube. The Buffer Solution contains the signal amplification polymers for *C. albicans* and *G. vaginalis*. Tubes are mixed by flicking briskly 10 times. The swabs are then expressed on the sides of the tube to remove fluid, and discarded. The tube cap is replaced with a filter tip. Samples processed in this manner must be assayed within twenty-four hours.

The Affirm VPIII Reagent Cassette has seven wells, six of which contain reagents. One Reagent Cassette is used per sample. Well 1 is empty, and the prepared sample is added to this well. Well 2 contains a Hybridization solution comprised of the biotinylated detector probes and formamide in a buffered chaotropic solution. Well 3 contains a Wash Solution. Well 4 contains the streptavidin-horseradish peroxidase (SA-HRP) conjugate. Wells 5 and 6 both contain Wash Solution. Well 7 contains a buffered peroxide solution. Prior to running the test, four drops of Substrate Solution are added to Well 7. The substrate solution contains the indicator that reacts with the HRP to form the blue color, which is read visually. If a chemiluminescent indicator is used (for research purposes only), the Affirm Processor is stopped before the Probe Analysis Card (PAC) enters Well 7.

The Affirm VPIII Probe Analysis Card contains the three analyte-specific capture beads previously described. In addition, there is one Negative control bead and one Positive control bead. One PAC is used per sample.

Affirm VPIII Reagent Cassettes are opened and arranged on the Affirm Automated Processor, one cassette per sample. The sample tubes are dispensed into well 1 of the Reagent Cassette. If the calorimetric, or visual detection method is used, four drops of Substrate Solution are added to Well 7. If a chemiluminescent detection method is to be used (for research purposes), then Substrate Solution is not added to Well 7. PACs are placed in well 1 of the Reagent Cassettes and the Processor is started.

The Processor arm picks up the PAC and gently agitates the card in the wells using a vertical, up-down motion. After several minutes in Well 1, the processor moves the PAC to well 2. If rRNA is present in the capture beads, the biotinylated detector probes in well 2 will hybridize to the bead-RNA complex. The Positive control bead is derivatized with a capture oligonucleotide that is complementary to one of the detector oligonucleotides in Well 7. This ensures that the positive control bead is always positive, unless the assay fails at the detection step. If the Positive control fails, it is a good indication that either 1) the user did not add the Substrate solution to Well 7, or 2) that there was a reagent failure in the cassette. Conversely, the Negative control bead is derivatized with an oligonucleotide that does not have a complementary detector oligonucleotide in any of the wells. Therefore, this bead should always remain colorless. After Well 2, the Processor moves the PAC to Well 3, where Wash Solution removes any non-specifically bound nucleic acid or oligonucleotide probes. In Well 4, the biotinylated detector probes bind to the SA-HRP conjugate. The PAC is then washed in two successive Wells, 5 and 6. This ensures that there will be no non-specific color development due to carryover of horseradish peroxidase. At this point the bead/nucleic-acid/detector/SA-HRP complex can be removed for chemiluminescent detection, or allowed to proceed to Well 7 for reaction with the Indicator substrate. The PAC is then briefly washed in Well 6, and the assay is completed. Any blue color development on the specific analyte beads indicates that the sample contains that organism. A colorless specific analyte bead indicates that the sample is negative for that organism.

Samples were processed and tested according to the Affirm VPIII Microbial Identification Test protocol unless otherwise noted.

EXAMPLE 2

Description of the Experimental Procedure for Evaluating Preservative Solutions

Pools of vaginal fluid were prepared from fresh, self-collected vaginal swabs and/or frozen vaginal swabs. Fresh swab donors were instructed to place their swabs (5 per donor) on ice within 2 hours of collection. Swabs were kept on ice until pools were prepared, within two hours, or they were frozen immediately for later use. To prepare the vaginal pools, ten fresh or thawed frozen swabs were expressed per milliliter of Normal Saline (Cat. No. 4397753, Becton Dickinson Microbiology Systems, Sparks Md.). Swabs were prepared in this manner until enough volume was obtained for the number of experimental samples being tested. A portion of the pool was used to resuspend organism pellets, as described below, and a portion was left uninoculated, to serve as the control.

*Candida albicans* (ATCC 60193) was grown on Sabouraud Dextrose agar (Cat. No. 4321278, Becton Dickinson Microbiology Systems, Sparks Md.) at 35° C. for 24–48 hours. A single colony was picked and streaked to a second plate, which was incubated for 18–20 hours at 35° C. After incubation, 3 mL of BSA/saline was added to the plate, and the colonies were gently resuspended with a 10 uL inoculation loop. A sterile pipet was used to transfer the suspension to a tube containing at least 10 mL of BSA/saline. The suspension was vortexed and measured spectrophotometrically for absorbance at 625 nm. The suspension was adjusted to an $OD_{625}$ of approximately 0.4 (approximately $6.0 \times 10^6$ CFU/mL). A volume of the suspension was then centrifuged for 10 minutes at 3000 rpm in a TJ-6 tabletop centrifuge (Beckman Instruments). The supernatant was decanted and the pellet was resuspended with the vaginal fluid to achieve a final concentration of approximately $7.5 \times 10^6$ CFU/mL.

*Gardnerella vaginalis* (ATCC 49145) was grown on Chocolate II agar (Cat. No. 4321267, Becton Dickinson) at 35° C. for 24–48 hours. Single colonies were picked and streaked to secondary plates, which were incubated for 18–48 hours at 35° C. After incubation, 3 mL of BSA/saline was added to each secondary plate, and the colonies were gently resuspended with a 10 uL inoculation loop. A sterile pipet was used to transfer the suspension to a tube containing at least 10 mL of BSA/saline. The suspension was vortexed and measured spectrophotometrically for absorbance at 625 nm. The suspension was adjusted to an $OD_{625}$ of approximately 0.3 (approximately $2.5 \times 10^8$ CFU/mL). A volume of the suspension was then centrifuged for 10 minutes at 3000 rpm in a TJ-6 tabletop centrifuge (Beckman Instruments). The supernatant was decanted and the pellet was resuspended with the vaginal fluid to achieve a final concentration of approximately $2.5 \times 10^9$ CFU/mL.

*Trichomonas vaginalis* (ATCC 30001) was grown in 10 mL tubes of Modified Diamond's Medium (Cat. No. 07-097, Remel) at 37° C. in 5–10% $CO_2$ for five days or until it reached a density of approximately $2 \times 10^5$ cells/mL. Secondary cultures were prepared from cultures that contained $1 \times 10^5$ to $1.5 \times 10^6$ Trichomonads/mL and were free of contamination. Fresh, pre-warmed tubes of medium were inoculated with 0.5 to 1.0 ml of the culture. Tubes were capped loosely and incubated for 2 to 3 days at 37° C. in 5–10% $CO_2$. Secondary cultures that were at least $2 \times 10^5$ Trichomonads/mL were pooled, mixed and counted using a hemacytometer. The suspension was spun for seven minutes at 2000 rpm in a TJ-6 tabletop centrifuge. The supernatant was decanted and the pellet was resuspended with the vaginal fluid to achieve a final concentration of approximately $6 \times 10^6$ Trichomonads/mL.

Typically, all three organisms were tested in an experiment. In this case, the pellets of each organism, *C. albicans*, *G. vaginalis* and *T vaginalis* were sequentially resuspended with the same vaginal fluid. Serial ten-fold dilutions of the spiked vaginal fluid were plated in duplicate on Chocolate II agar plates to determine actual viable cfu/mL concentrations of *Gardnerella vaginalis* and *Candida albicans*.

Glass screw capped tubes, or Affirm VPIII sample tubes were prepared by pipetting 100 uL of the preservative/fixative solution under test into the tubes. Nothing was pipetted into negative control (no preservative) tubes. Three replicates were prepared for each test condition and each time point. Affirm Sample Collection swabs (Cat. No. 4406251) were seeded with 100 ul of vaginal fluid, or spiked vaginal fluid. Swabs were then placed into the glass or Affirm VPIII tubes and capped. Initial time point samples, $t_o$, were processed immediately. The remaining samples were processed at approximately 24, 48, 72 or 96 hours later. Testing proceeded according to the protocol described in Example 1.

For quantitative detection, a chemiluminescent substrate was used. The detection substrate was lumino/4-iodophenol (Boehringer-Mannheim Chemiluminescence ELISA Substrate, catalog no. 1582950). Briefly, PACs were removed from the Affirm Processor just prior to entering Well 7. Capture beads were removed for the PACs and placed into white, flat-bottomed microtiter wells, one bead per well. The recipient wells contained 100 ul of Wash Solution, to keep the beads from drying out. Once the plate was full, the Wash Solution was aspirated from the wells using a multi-channel pipet, and 100 ul of the chemiluminescent substrate solution was added per well. The plate was immediately placed on a plate reader (Dynatek ML3000, internal temperature 30° C., 7 cycles, 61 second pause between cycles) and read for 7 cycles. Data from the $5^{th}$ cycle (approximately ten minutes after the addition of substrate) was used for all analyses.

EXAMPLE 3

Common Fixatives and Preservatives Tested for Usefulness with Affirm Samples

The following table lists a number of commercially available preservatives and fixatives or solutions prepared in-house using standard formulations. These solutions were tested in the Affirm VPIII Microbial Identification Test with samples prepared according to the protocol described in EXAMPLE 2, using glass sample tubes and chemiluminescent detection. Solutions that failed to provide at least 24 hours of sample stability are designated as "FAILED", while solutions that interfered with the Affirm assay are designated as "INTERFERED".

| Reagent | Manufacturer | Status |
| --- | --- | --- |
| PreservCyt (50% Methanol, Acetic Acid, EDTA) | Cytyc | FAILED |
| 95% Methanol, Acetic Acid, EDTA | Prep'd in house | FAILED |
| 95% Methanol, Acetic Acid, EDTA, Lithium Chloride | Prep'd in house | FAILED |
| 95% Methanol, Acetic Acid | Prep'd in house | FAILED |
| 95% Methanol, EDTA | Prep'd in house | FAILED |
| 95% Methanol | Prep'd in house | FAILED |
| Buffered Formalin | SDL Inc. | FAILED |
| Parasafe | SDL Inc. | FAILED |
| PVA (low density poly vinyl alcohol) | SDL Inc. | Interfered |
| Affirm VPIII Buffer | Prep'd in house | FAILED |
| Modified Affirm Buffer (0.5x, with Lithium Chloride) | Prep'd in house | FAILED |
| Carnoy's solution (60% ethanol, 30% chloroform, 10% acetic acid) | Prep'd in house | Interfered |
| Acid/Ethanol (80% ethanol, 20% acetic acid) | Prep'd in house | FAILED |
| PACE Transport Buffer | Gen-Probe | FAILED |
| RNA Later | Ambion | FAILED |
| Molecular Biology Fixative | Streck Labs. | FAILED |
| CytoRich Blue Preservative Fluid | AutoCyte, Inc | FAILED |

EXAMPLE 4

Preservative Effects of Three Formulations Over Twenty-Four Hours

Three formulations of methanol and dimethyl sulfoxide solution were prepared and tested for their preservative ability over twenty four hours with *C. albicans, G. vaginalis* and *T vaginalis*. The procedure was as described in Example 2, using glass sample tubes. Organism cfu per ml of vaginal fluid were as follows: Trichomonas, $6 \times 10^6$ mL; Gardnerella, $1.5 \times 10^9$/mL; Candida, $1 \times 10^7$/mL. Signal was measured using chemiluminescent detection methods, as described in Example 2. Reported values (Relative Luminescence Units, RLUs) are the mean of three replicates.

| Solution | Hours | Negative | Positive | Tv | Gv | Ca |
|---|---|---|---|---|---|---|
| None | 0 | 0.0 | 6.8 | 5.3 | 154.4 | 11.3 |
| | 24 | 0.5 | 9.7 | 0.1 | 77.5 | 2286.9 |
| 80% Methanol, 20% DMSO | 0 | 0.0 | 9.8 | 5.9 | 103.8 | 15.8 |
| | 24 | 0.0 | 9.3 | 6.4 | 102.0 | 15.3 |
| 50% Methanol, 50% DMSO | 0 | 0.1 | 10.3 | 5.8 | 171.5 | 22.4 |
| | 24 | 0.0 | 9.7 | 5.9 | 196.1 | 15.1 |
| 100% Methanol | 0 | 0.0 | 10.6 | 7.0 | 172.7 | 16.7 |
| | 24 | 0.0 | 9.8 | 7.1 | 106.9 | 16.4 |

The data demonstrated that with no preservative solution, *T. vaginalis* signal was negative, *G. vaginalis* signal sharply declined, and *C. albicans* signal sharply increased (due to growth) by 24 hours. With the preservative solutions, signals remained relatively constant over 24 hours of ambient temperature storage of the samples.

EXAMPLE 5

Preservative Effect of Additional Formulations Over Twenty-Four Hours

Additional formulations of preservative solution were tested for their preservative ability over twenty four hours with *C. albicans* and *G. vaginalis*. The procedure was as described in Example 2, using glass sample tubes. Organism cfu per ml of vaginal fluid were as follows: Gardnerella, $9.7 \times 10^8$/mL; Candida, $3.4 \times 10^6$/mL. Signal was measured using chemiluminescent detection methods, as described in Example 2. Reported values (Relative Luminescence Units, RLUs) are the mean of three replicates.

| Solution | Hours | Negative | Positive | Gv | Ca |
|---|---|---|---|---|---|
| None | 0 | 0.0 | 8.2 | 140.4 | 15.7 |
| | 24 | 0.0 | 10.3 | 71.0 | 1721.1 |
| 40% Methanol, 40% Ethanol, 20% DMSO | 0 | 0.0 | 8.9 | 52.3 | 10.4 |
| | 24 | 0.0 | 9.8 | 95.2 | 12.1 |
| 25% Methanol, 25% Ethanol, 50% DMSO | 0 | 0.0 | 10.0 | 124.0 | 16.8 |
| | 24 | 0.0 | 9.7 | 165.7 | 15.8 |
| 80% Ethanol, 20% DMSO | 0 | 0.1 | 9.9 | 127.2 | 16.1 |
| | 24 | 0.0 | 10.2 | 102.2 | 13.1 |

The data indicated that with no preservative solution *G. vaginalis* signal sharply declined, and *C. albicans* signal sharply increased (due to growth) by 24 hours. With the preservative solutions, signals remained relatively constant over 24 hours of ambient temperature storage of the samples.

EXAMPLE 6

Sample Stability at Forty-Eight Hours with Several Formulations

Five preservative formulations were tested for their preservative ability over forty eight hours with *T. vaginalis*, *C. albicans* and *G. vaginalis*. The procedure was as described in Example 2, using glass sample tubes. Organism cfu per ml of vaginal fluid were as follows: Trichomonas, $4.7 \times 10^7$/mL; Gardnerella, $1.4 \times 10^8$/mL; Candida, $5.6 \times 10^7$/ml. Signal was measured using chemiluminescent detection methods, as described in Example 2. Reported values (Relative Luminescence Units, RLUs) are the mean of three replicates.

| Solution | Hours | Negative | Positive | Tv | Gv | Ca |
|---|---|---|---|---|---|---|
| None | 0 | 0.0 | 9.5 | 87.0 | 190.0 | 16.8 |
| | 24 | 0.0 | 8.1 | 9.1 | 16.7 | 1528.9 |
| | 48 | 0.0 | 9.6 | 0.6 | 1.7 | 1394.9 |
| 80% Methanol, 20% DMSO | 0 | 0.0 | 10.2 | 68.4 | 70.1 | 8.1 |
| | 24 | 0.0 | 9.4 | 66.3 | 171.6 | 4.8 |
| | 48 | 0.0 | 8.8 | 75.3 | 127.4 | 6.8 |
| 50% Methanol, 50% DMSO | 0 | 0.1 | 8.8 | 68.7 | 79.6 | 7.5 |
| | 24 | 0.0 | 11.0 | 67.7 | 162.1 | 5.9 |
| | 48 | 0.0 | 8.4 | 79.5 | 174.9 | 5.7 |
| 40% Methanol, 40% Ethanol, 20% DMSO | 0 | 0.0 | 8.1 | 87.6 | 179.4 | 7.8 |
| | 24 | 0.0 | 10.0 | 75.3 | 136.2 | 4.8 |
| | 48 | 0.0 | 8.4 | 70.7 | 75.5 | 5.4 |
| 25% Methanol, 25% Ethanol, 50% DMSO | 0 | 0.0 | 9.0 | 96.2 | 228.8 | 7.9 |
| | 24 | 0.0 | 8.1 | 67.4 | 132.7 | 2.7 |
| | 48 | 0.0 | 8.4 | 70.8 | 124.6 | 5.0 |
| 80% Ethanol, 20% DMSO | 0 | 0.0 | 9.1 | 97.4 | 128.0 | 8.2 |
| | 24 | 0.0 | 9.4 | 66.1 | 117.2 | 2.7 |
| | 48 | 0.0 | 8.9 | 70.2 | 84.8 | 5.4 |

The data indicated that with no preservative solution *T. vaginalis* and *G. vaginalis* signals were negative at 48 hours, and *C. albicans* signal was sharply increased (due to growth) BY 24 and 48 hours. With the preservative solutions, signals remained relatively constant over 48 hours of ambient temperature storage of the samples.

EXAMPLE 7

Sample Stability with Preservative in the Affirm VPIII Sample Tube

One preservative formulation was tested over forty eight hours with *T. vaginalis*, *C. albicans* and *G. vaginalis*, using either glass screw capped tubes or the low density polyethylene Affirm VPIII processing tube. The procedure was as described in Example 2. Organism cfu per ml of vaginal fluid were as follows: Trichomonas, $3.9 \times 10^7$/mL; Gardnerella, $3.1 \times 10^8$/mL; Candida, $5.3 \times 10^6$/mL. Signal was measured using chemiluminescent detection methods, as described in Example 2. Reported values (Relative Luminescence Units, RLUs) are the mean of three replicates.

| Solution | Tube | Hours | Negative | Positive | Tv | Gv | Ca |
|---|---|---|---|---|---|---|---|
| None | Glass | 0 | 0.0 | 8.5 | 47.5 | 164.5 | 7.9 |
| | | 24 | 0.0 | 9.7 | 1.2 | 20.1 | 1093.0 |
| | | 48 | 0.0 | 10.9 | 0.1 | .8 | 1583.0 |
| | Affirm | 0 | 0.0 | 7.8 | 85.4 | 204.1 | 13.1 |
| | | 24 | 0.0 | 9.5 | 8.3 | 98.6 | 857.3 |
| | | 48 | 0.0 | 10.2 | 3.0 | 1.5 | 1152.5 |
| 50% Methanol, 50% DMSO | Glass | 0 | 0.0 | 8.7 | 43.9 | 202.7 | 6.2 |
| | | 24 | 0.0 | 9.9 | 41.9 | 292.7 | 4.1 |
| | | 48 | 0.0 | 9.3 | 39.5 | 296.4 | 5.8 |
| | Affirm | 0 | 0.0 | 8.5 | 119.3 | 476.7 | 4.4 |
| | | 24 | 0.2 | 10.1 | 109.4 | 725.7 | 5.4 |
| | | 48 | 0.0 | 11.7 | 116.5 | 890.5 | 5.0 |

The results indicated that the Affirm VPIII sample tube offered stability comparable to the glass screw capped tubes when preservative solution was used. In fact, less sample was lost using the Affirm VPIII tube because the swab was transported and processed in the same tube. Swabs transported in glass tubes were transferred to Affirm VPIII tubes for processing. Neither tube maintained sample stability when no preservative solution was used.

EXAMPLE 8

Solution Performance Across Sample Matrix Pools

An experiment was performed to demonstrate the preservative solution performance across different vaginal fluid matrices. Four pools of vaginal fluid were prepared: two from freshly collected swabs and two from frozen swabs. Affirm VPIII tubes were used for sample transport conditions. The procedure was as described in Example 2. The average organism cfu per ml of vaginal fluid was as follows: Trichomonas, $5 \times 10^7$/mL; Gardnerella, $2.1 \times 10^8$/mL; Candida, $5.6 \times 10^7$/mL. Signal was measured using chemiluminescent detection methods, as described in Example 2. Reported values (Relative Luminescence Units, RLUs) are the mean of three replicates.

| Vaginal pool | Solution | Hours | Negative | Positive | Tv | Gv | Ca |
|---|---|---|---|---|---|---|---|
| Pool 1 (frozen) | None | 0 | 0.0 | 7.5 | 83.3 | 141.5 | 27.5 |
| | | 24 | 0.1 | 12.9 | 14.2 | 78.7 | 1255.8 |
| | | 48 | 0.0 | 8.9 | 1.9 | 4.4 | 751.2 |
| | | 72 | 0.1 | 18.8 | 0.8 | 7.7 | 2619.2 |
| | 50% MeOH, 50% DMSO | 0 | 0.0 | 8.8 | 68.1 | 245.7 | 12.1 |
| | | 24 | 0.0 | 10.5 | 58.9 | 249.4 | 24.3 |
| | | 48 | 0.0 | 9.4 | 56.1 | 299.9 | 13.5 |
| | | 72 | 0.0 | 8.1 | 31.1 | 222.3 | 20.2 |
| Pool 2 (frozen) | None | 0 | 0.0 | 7.6 | 93.8 | 89.0 | 20.8 |
| | | 24 | 0.0 | 9.7 | 7.8 | 32.7 | 1316.3 |
| | | 48 | 0.0 | 7.3 | 1.5 | 1.8 | 955.4 |
| | | 72 | 0.0 | 9.6 | 0.2 | 2.4 | 1773.7 |
| | 50% MeOH, 50% DMSO | 0 | 0.0 | 6.7 | 99.3 | 168.7 | 9.2 |
| | | 24 | 0.1 | 11.0 | 94.2 | 168.2 | 13.5 |
| | | 48 | 0.0 | 9.1 | 76.5 | 143.3 | 9.9 |
| | | 72 | 0.0 | 9.3 | 60.2 | 221.3 | 11.1 |
| Pool 3 (fresh) | None | 0 | 0.0 | 8.6 | 86.9 | 76.3 | 17.1 |
| | | 24 | 0.0 | 9.2 | 0.0 | 8.4 | 1244.7 |
| | | 48 | 0.0 | 9.6 | 0.0 | 2.6 | 1135.8 |
| | | 72 | 0.0 | 8.9 | 0.0 | 0.9 | 1205.1 |
| | 50% MeOH, 50% DMSO | 0 | 0.0 | 5.6 | 79.2 | 118.6 | 6.1 |
| | | 24 | 0.2 | 9.2 | 95.7 | 155.8 | 11.6 |
| | | 48 | 0.0 | 9.2 | 62.8 | 107.8 | 6.4 |
| | | 72 | 0.0 | 7.5 | 54.4 | 159.4 | 9.2 |
| Pool 4 (fresh) | None | 0 | 0.0 | 8.2 | 68.9 | 119.6 | 18.5 |
| | | 24 | 0.0 | 7.9 | 0.7 | 54.4 | 1226.7 |
| | | 48 | 0.0 | 8.8 | 0.0 | 11.8 | 1086.9 |
| | | 72 | 0.0 | 6.0 | 0.0 | 2.6 | 1223.4 |
| | 50% MeOH, 50% DMSO | 0 | 0.0 | 9.5 | 94.0 | 172.6 | 11.2 |
| | | 24 | 0.0 | 8.3 | 44.9 | 144.0 | 9.6 |
| | | 48 | 0.0 | 6.3 | 45.9 | 135.9 | 5.1 |
| | | 72 | 0.0 | 7.1 | 29.8 | 147.1 | 6.7 |

The results showed that the solution was capable of maintaining signal of the organisms in the four vaginal fluid pools over 72 hours of storage time.

EXAMPLE 9

Solution Performance Across Sample Matrix From Fifteen Individuals

An experiment was performed to demonstrate the performance of the preservative solution (50% Methanol, 50% dimethyl sulfoxide) across vaginal fluid collected from fifteen women. Ten swabs were collected per day for two days from each donor. Affirm VPIII tubes were used for sample transport conditions. The procedure was as described in Example 2. The average organism cfu per ml of vaginal fluid was as follows: Trichomonas, $3.5 \times 10^7$/mL; Gardnerella, $6.0 \times 10^8$/mL; Candida, $7.7 \times 10^6$/mL. Signal was measured using chemiluminescent detection methods, as described in Example 2. Reported values (Relative Luminescence Units, RLUs) are the mean of three replicates.

| Donor | Hours | Negative | Positive | Tv | Gv | Ca |
|---|---|---|---|---|---|---|
| 1 | 0 | 0.0 | 7.8 | 47.1 | 165.0 | 15.3 |
| | 24 | 0.0 | 7.6 | 67.5 | 277.3 | 12.7 |
| | 48 | 0.0 | 12.8 | 47.3 | 249.0 | 16.0 |
| | 72 | 0.0 | 7.8 | 43.7 | 214.6 | 9.4 |
| 2 | 0 | 0.0 | 5.4 | 67.6 | 254.4 | 15.0 |
| | 24 | 0.0 | 6.4 | 91.8 | 464.6 | 27.8 |
| | 48 | 0.0 | 11.1 | 99.7 | 665.2 | 27.7 |
| | 72 | 0.0 | 9.5 | 61.6 | 485.7 | 16.2 |
| 3 | 0 | 0.0 | 8.6 | 72.4 | 268.7 | 16.5 |
| | 24 | 0.0 | 9.1 | 65.7 | 308.0 | 19.7 |
| | 48 | 0.0 | 14.8 | 81.8 | 449.7 | 28.6 |
| | 72 | 0.0 | 8.2 | 49.4 | 301.1 | 16.7 |
| 4 | 0 | 0.0 | 8.9 | 65.3 | 206.1 | 15.6 |
| | 24 | 0.0 | 8.7 | 39.0 | 203.4 | 18.8 |
| | 48 | 0.0 | 15.2 | 40.0 | 261.5 | 29.4 |
| | 72 | 0.0 | 6.4 | 23.6 | 216.7 | 13.3 |
| 5 | 0 | 0.0 | 9.3 | 57.6 | 165.3 | 11.8 |
| | 24 | 0.0 | 8.6 | 50.8 | 266.5 | 12.8 |
| | 48 | 0.1 | 12.1 | 64.6 | 299.9 | 24.0 |
| | 72 | 0.0 | 8.5 | 44.6 | 259.4 | 11.8 |
| 6 | 0 | 0.0 | 8.5 | 63.3 | 464.7 | 16.3 |
| | 24 | 0.0 | 7.1 | 40.9 | 259.0 | 10.4 |
| | 48 | 0.0 | 8.6 | 49.7 | 349.5 | 12.4 |
| | 72 | 0.0 | 8.1 | 44.9 | 486.6 | 15.9 |
| 7 | 0 | 0.0 | 8.9 | 62.6 | 318.1 | 20.0 |
| | 24 | 0.0 | 8.2 | 44.7 | 244.9 | 9.5 |
| | 48 | 0.0 | 8.4 | 34.7 | 226.1 | 9.5 |
| | 72 | 0.0 | 8.9 | 33.5 | 284.1 | 12.9 |
| 8 | 0 | 0.0 | 8.1 | 60.2 | 291.6 | 11.2 |
| | 24 | 0.0 | 7.9 | 42.3 | 168.2 | 7.5 |
| | 48 | 0.0 | 9.8 | 44.4 | 190.9 | 7.1 |
| | 72 | 0.0 | 8.9 | 53.1 | 292.6 | 8.9 |
| 9 | 0 | 0.0 | 8.6 | 62.2 | 273.6 | 17.6 |
| | 24 | 0.0 | 8.1 | 27.2 | 191.7 | 12.6 |
| | 48 | 0.0 | 8.6 | 21.3 | 222.8 | 16.7 |
| | 72 | 0.0 | 12.0 | 29.1 | 379.5 | 16.7 |
| 10 | 0 | 0.0 | 8.3 | 39.8 | 145.7 | 12.2 |
| | 24 | 0.1 | 7.5 | 26.5 | 103.7 | 8.9 |
| | 48 | 0.2 | 9.9 | 22.9 | 128.0 | 11.0 |
| | 72 | 0.0 | 9.2 | 31.1 | 208.9 | 14.1 |
| 11 | 0 | 0.0 | 8.5 | 113.2 | 218.7 | 8.2 |
| | 24 | 0.0 | 8.1 | 95.6 | 156.6 | 5.1 |
| | 48 | 0.0 | 11.9 | 158.2 | 332.6 | 8.2 |
| | 72 | 0.0 | 8.6 | 90.8 | 178.2 | 3.0 |
| 12 | 0 | 0.0 | 9.5 | 112.4 | 189.7 | 11.7 |
| | 24 | 0.0 | 8.6 | 66.0 | 172.4 | 11.9 |
| | 48 | 0.0 | 13.2 | 114.6 | 346.8 | 22.0 |
| | 72 | 0.0 | 9.8 | 60.4 | 170.4 | 7.5 |
| 13 | 0 | 0.0 | 9.8 | 130.2 | 159.9 | 7.3 |
| | 24 | 0.0 | 10.0 | 118.5 | 191.4 | 10.2 |
| | 48 | 0.0 | 13.2 | 222.4 | 322.2 | 14.7 |
| | 72 | 0.0 | 9.0 | 125.0 | 225.3 | 7.8 |
| 14 | 0 | 0.0 | 8.6 | 118.7 | 138.7 | 9.7 |
| | 24 | 0.0 | 8.7 | 91.2 | 126.1 | 6.0 |
| | 48 | 0.0 | 15.2 | 160.6 | 213.9 | 12.3 |
| | 72 | 0.0 | 9.3 | 89.5 | 105.5 | 4.3 |
| 15 | 0 | 0.0 | 10.1 | 103.2 | 97.8 | 7.5 |
| | 24 | 0.0 | 8.7 | 88.0 | 123.5 | 11.9 |
| | 48 | 0.0 | 14.6 | 122.6 | 168.6 | 18.1 |
| | 72 | 0.0 | 9.3 | 97.8 | 117.7 | 10.8 |

The solution demonstrated preservative effects across the vaginal fluid from 15 different iindividual donors. All organism signals were maintained.

EXAMPLE 10

Solution Performance with Samples Stored at a Range of Temperatures

An experiment was performed to demonstrate the performance of the preservative solution (50% Mithanol, 50% demethyl sulfoxide) across a range of storage temperatures. Ten swabs were collected per day for two days from each donor. Affirm VPIII tubes were used for sample transport conditions. The procedure was as described in Example 2. Organism cfu per ml of vaginal fluid were as follows: Trichomonas, $8.2\times10^6$/mL; Gardnerella, $1.4\times10^7$/ml. $7.9\times10^6$/mL. Signal was measured using colorimetric detection methods, described in Example 2, except the bead color was assigned a value relative to the positive control bead color. Positive control beads were assigned a "2". Analyte beads darker than the control bead were assigned a "3", analyte beads the same color as the control bead were assigned a "2", and analyte beads lighter than the control bead, but darker than the negative control bead, were assigned a "1". Reported values are the mode of three replicates, each scored by three different readers. Samples were stored up to 96 hours.

| Solution | Temperature | Hours | Negative | Positive | Tv | Gv | Ca |
|---|---|---|---|---|---|---|---|
| None | Ambient | 0 | 0 | 2 | 3 | 2 | 3 |
| | | 24 | 0 | 2 | 0 | 0 | 3 |
| | | 48 | 0 | 2 | 0 | 0 | 3 |
| | | 96 | 0 | 2 | 0 | 0 | 3 |
| 50% Methanol, 50% DMSO | Ambient | 0 | 0 | 2 | 3 | 3 | 3 |
| | | 24 | 0 | 2 | 3 | 3 | 3 |
| | | 48 | 0 | 2 | 2 | 2 | 3 |
| | | 96 | 0 | 2 | 2 | 3 | 3 |
| | 2° C. | 0 | 0 | 2 | 3 | 3 | 3 |
| | | 24 | 0 | 2 | 3 | 3 | 3 |
| | | 48 | 0 | 2 | 3 | 3 | 2 |
| | | 96 | 0 | 2 | 3 | 3 | 2 |
| | 30° C. | 0 | 0 | 2 | 3 | 3 | 3 |
| | | 24 | 0 | 2 | 2 | 2 | 2 |
| | | 48 | 0 | 2 | 2 | 2 | 3 |
| | | 96 | 0 | 2 | 1 | 1 | 1 |
| | 35° C. | 0 | 0 | 2 | 3 | 3 | 3 |
| | | 24 | 0 | 2 | 2 | 3 | 2 |
| | | 48 | 0 | 2 | 1 | 3 | 2 |
| | | 96 | 0 | 2 | 2 | 3 | 3 |

The data showed that the solution was capable of providing sample stability at a range of storage temperatures over 96 hours. It also indicated that the preservative solution did not have an effect on the method of detection.

EXAMPLE 11

Demonstration That the Solution Provides Protection Against Nucleases

The preferred embodiment (50% Methanol, 50% DMSO) was tested for its ability to protect RNA against nuclease degradation. A commercially available RNase detection kit (RNaseAler™RNase Detection Dipsticks, catalog no 1960, Ambion) was used with samples of vaginal fluid alone and vaginal fluid with preservative solution added. The kit provides an RNA solution that is spotted onto a dipstick in two places, according to kit protocol. One spot is incubated with the test solution. Both spots on the dipstick are then subjected to colorimetric detection. If the RNA spot that was incubated with the test solution is white or a lighter shade of blue than the control spot, the test solution contains RNase. The strips were used to test vaginal fluid that had been mixed with the preservative solution. The results indicated that the vaginal fluid mixed with preservative solution left detectable RNA on the test spot more often than untreated vaginal fluid. This indicated that the preservative solution provided protection against nucleases present in the vaginal fluid.

In a separate experiment, the RNaseAlert™RNase Detection Dipsticks were used to assess the preservative solution with human whole blood, serum and plasma. Samples of each were mixed 1:1 with the preferred embodiment (50% methanol, 50% DMSO) and tested with the dipsticks. Samples containing no preservative were tested as well. The results indicated that the whole blood, serum and plasma samples contained active RNases, since no visible spot remained on the test strip after the protocol was completed. However, when whole blood, serum and plasma were mixed with the preservative solution, the test RNA spot was clearly visible on the strip. This demonstrated that the preservative solution provided protection against nucleases present in human whole blood, serum and plasma.

EXAMPLE 12

Performance Over a Broad Range of Solution Compositions

An experiment was performed to demonstrate the performance of the preservative solution when either component was varied to extreme concentrations. Samples were stored in the preservative for up to 72 hours. Affirm VPIII tubes were used for sample transport conditions. The procedure was as described in Example 2. Organism cfu per ml of vaginal fluid were as follows: Trichomonas, $1\times10^7$/mL; Gardnerella, $1.9\times10^7$/mL; Candida, $1.4\times10^7$/mL. Signal was measured using colorimetric detection methods, as described in Example 10 Reported values are the average of three replicates, each scored by three different readers. Preservative effects were observed for all formulations tested.

| Formulation | Hours | Negative | Positive | Tv | Gv | Ca |
|---|---|---|---|---|---|---|
| None | 0 | 0 | 2 | 3 | 1 | 3 |
| | 24 | 0 | 2 | 1 | 0 | 4 |
| | 72 | 0 | 2 | 0 | 0 | 4 |
| 20% Methanol 80% DMSO | 0 | 0 | 2 | 3 | 2 | 3 |
| | 24 | 0 | 2 | 3 | 2 | 3 |
| | 72 | 0 | 2 | 2.9 | 1.7 | 3 |
| 40% Methanol 60% DMSO | 0 | 0 | 2 | 3 | 2 | 3 |
| | 24 | 0 | 2 | 3 | 2 | 3 |
| | 72 | 0 | 2 | 3 | 2.2 | 3 |
| 50% Methanol 50% DMSO | 0 | 0 | 2 | 3 | 2 | 3 |
| | 24 | 0 | 2 | 3 | 2 | 3 |
| | 72 | 0 | 2 | 3 | 2 | 3 |
| 60% Methanol 40% DMSO | 0 | 0 | 2 | 3 | 2 | 3 |
| | 24 | 0 | 2 | 3 | 2 | 3 |
| | 72 | 0 | 2 | 3 | 2 | 3 |
| 80% Methanol 20% DMSO | 0 | 0 | 2 | 3 | 2 | 3 |
| | 24 | 0 | 2 | 3 | 2 | 3 |
| | 72 | 0 | 2 | 3 | 1.2 | 3 |
| 100% Methanol | 0 | 0 | 2 | 3 | 2 | 3 |
| | 24 | 0 | 2 | 2.9 | 2 | 3 |
| | 72 | 0 | 2 | 3 | 1.8 | 3 |
| 100% DMSO | 0 | 0 | 2 | 3 | 2 | 3 |
| | 24 | 0 | 2 | 3 | 2 | 3 |
| | 72 | 0 | 2 | 3 | 2 | 3 |

EXAMPLE 13

Microscopic Evaluation of Cells Treated with Preservative Solution

Cells from various organisms were pelleted by centrifugation and then resuspended in BSA/saline. An aliquot of each cell suspension was treated with an equal volume of preservative solution comprised of a 1:1 mixture of methanol and DMSO. The treated cells were stored at ambient temperatures for 24 hours. As a control, a second aliquot of cells was treated with an equal volume of BSA/saline immediately before microscopic examination. Both aliquots were examined using a phase contrast microscope (Eclipse E400, Nikon Japan) under 40×power.

Figures 2, 2A:
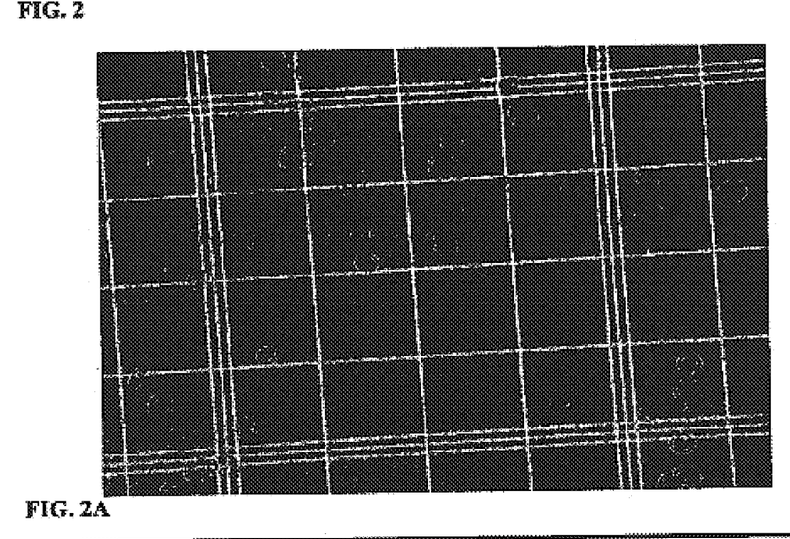
FIG. 2A is a micrograph showing untreated *T. vaginalis* cells as compared to FIG. 2B showing a micrograph of *T vaginalis* cells treated with a composition of the present invention.
Figure 2B:
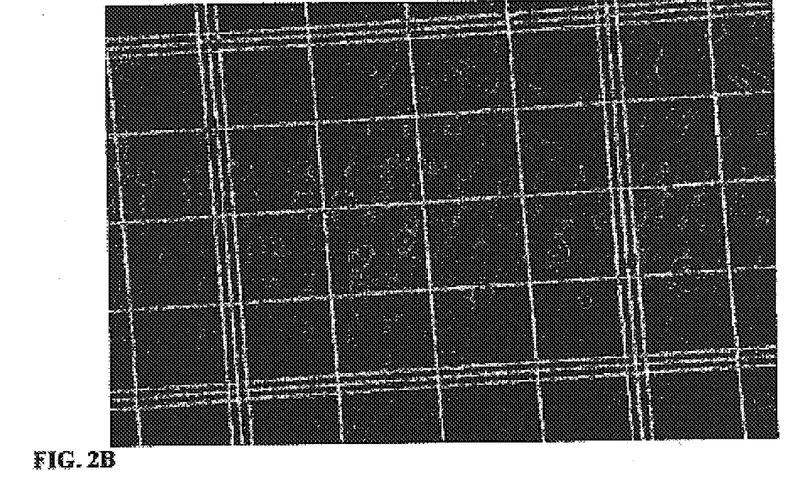
Figures 3, 3A:
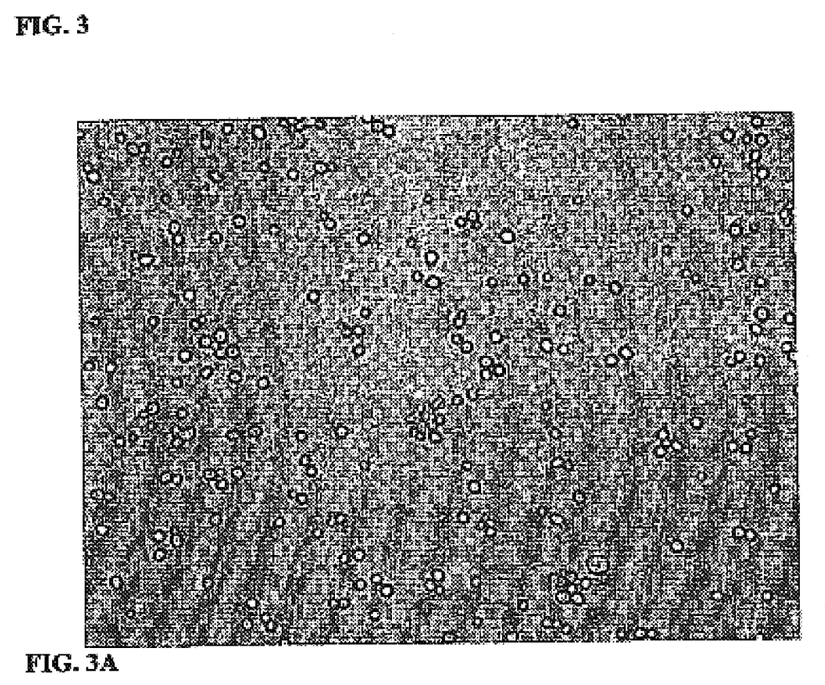
FIG. 3A is a micrograph showing untreated *C albicans* cells as compared to FIG. 3B showing a micrograph of *C. albicans* cells treated with a composition of the present invention.
Figure 3B:
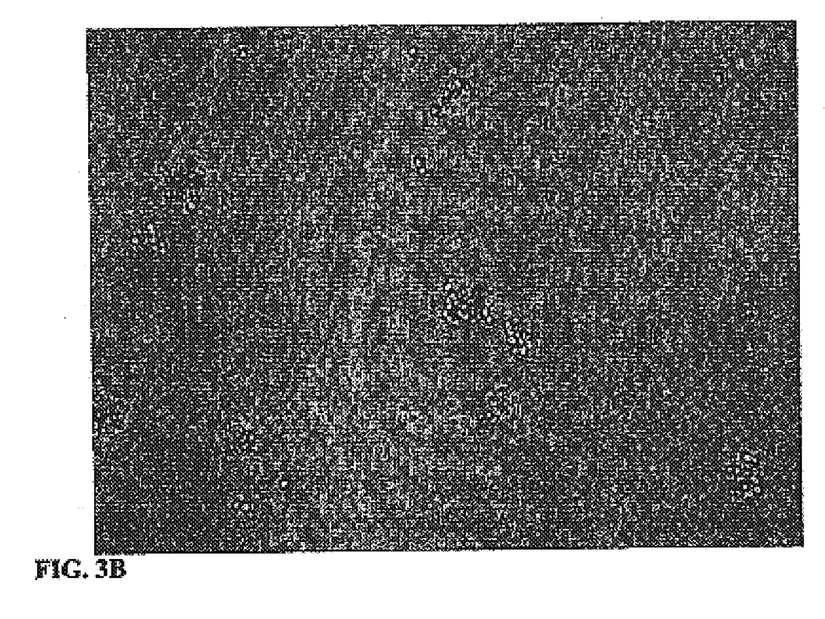
Figures 4, 4A:
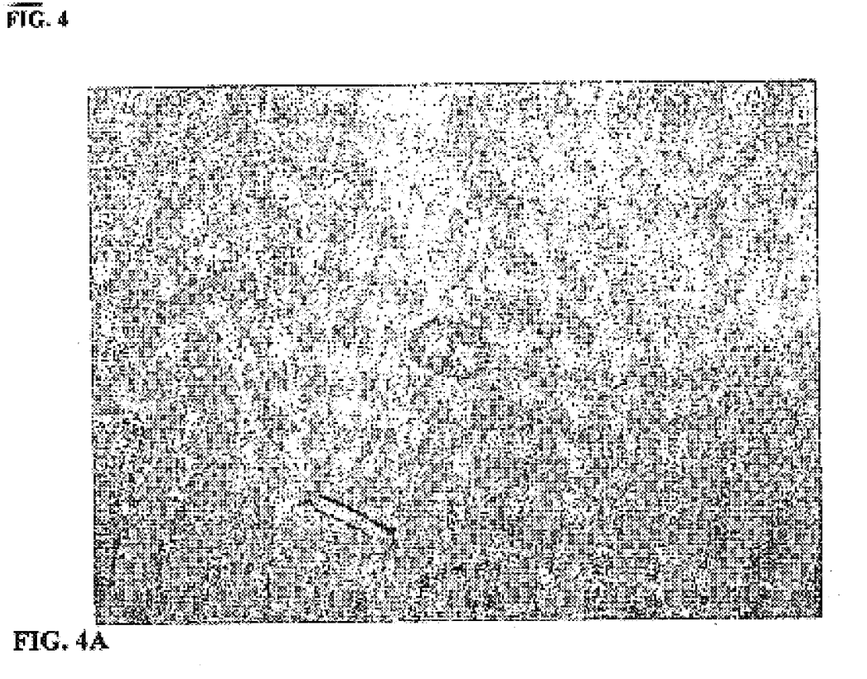
FIG. 4A is a micrograph showing untreated human epidermal keratinocytes as compared to FIG. 4B showing a micrograph of human epidermal keratinocytes treated with a composition of the present invention.
Figure 4B:
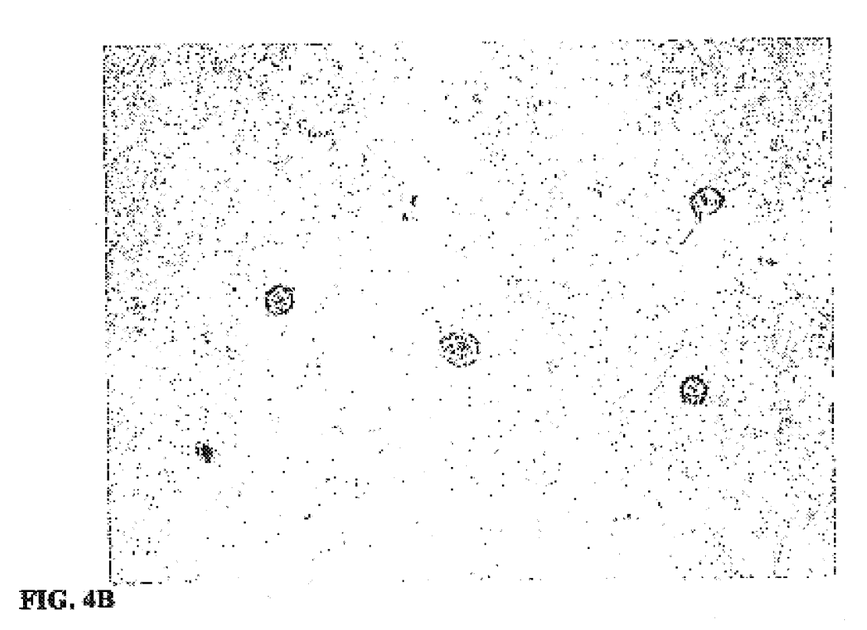
Figures 5, 5A:
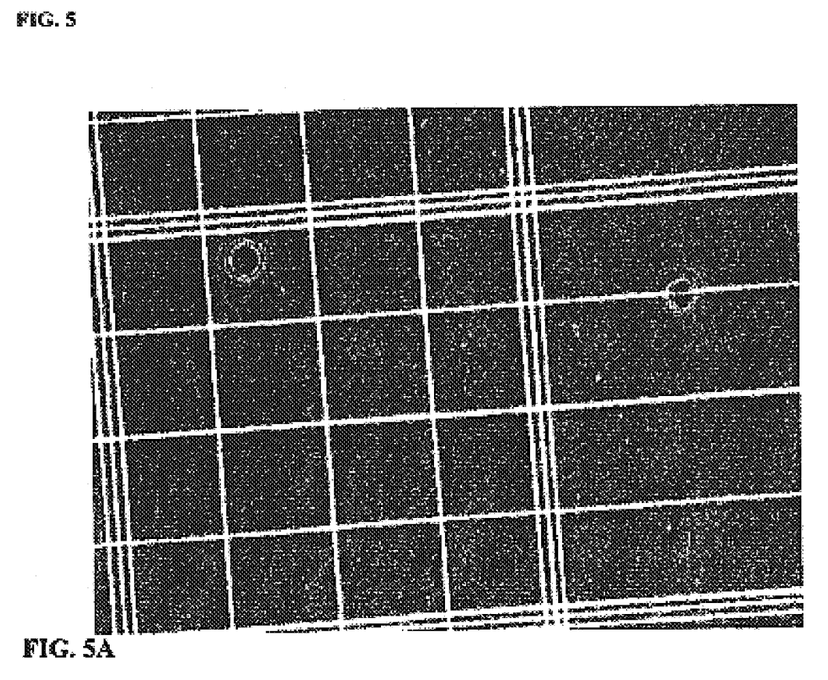
FIG. 5A is a micrograph showing untreated *Spodoptera frugiperda* ovarian cells as compared to FIG. 5B showing a micrograph of *Spodoptera frugiperda* ovarian cells treated with a composition of the present invention.
Figure 5B:
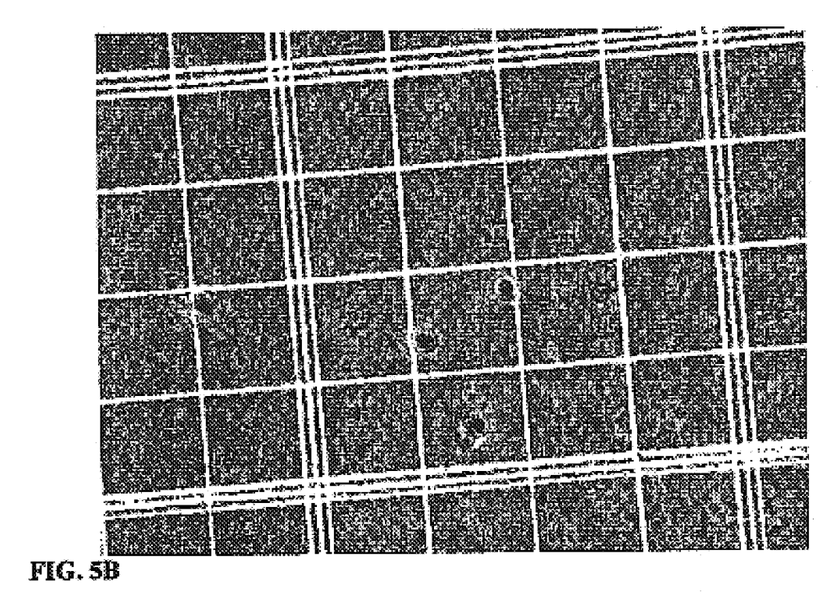
Figures 6, 6A:
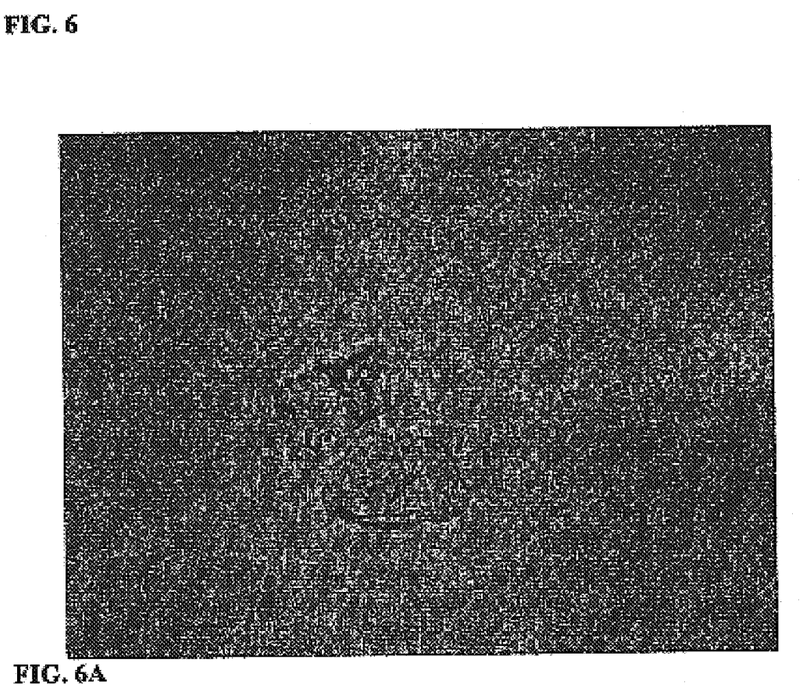
FIG. 6A is a micrograph showing untreated human buccal cells as compared to FIG. 6B showing a micrograph of human buccal cells treated with a composition of the present invention.
Figure 6B:
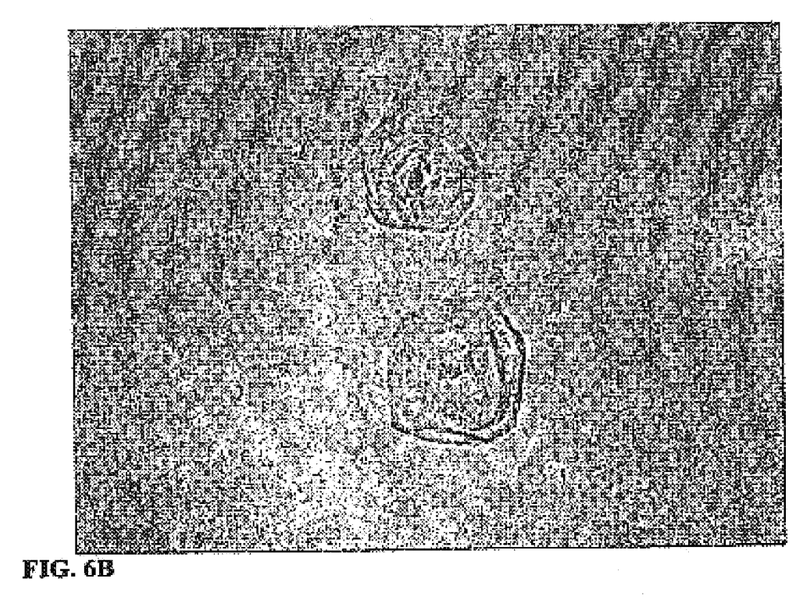

| Cell | Origin | Results |
|---|---|---|
| *Trichomonas vaginalis* | ATCC 30001 | FIGS. 2a and 2b |
| *Candida albicans* | ATCC 60193 | FIGS. 3a and 3b |
| Human epidermal keratinocytes | Cell line NHEK-3007 (BioWhittaker Cat. No. CC-2503) | FIGS. 4a and 4b |
| *Spodoptera frugiperda* ovarian cells | Sf9 insect cell line (PharMingen Cat. No. 21300L) | FIGS. 5a and 5b |
| Human buccal cells | Cheek scrapings | FIGS. 6a and 6b |

Microscopic examination revealed cells that were visually intact after 24 hours of ambient storage in the preservative solution. Cells were similar in appearance and number to the untreated controls. These results indicate that the solution does not lyse the cells, but stabilizes their structure and keeps the cells intact.

What is claimed is:

1. A composition for stabilizing the nucleic acids of at least one cell in a specimen at ambient temperature, said composition being comprised of:
   (a) a first substance capable of precipitating or denaturing proteins, comprising at least one first alcohol or ketone and a second alcohol or ketone whose concentration is less than 80% of the total composition; and
   (b) dimethyl sulfoxide whose concentration is greater than 20% of the total composition, wherein the concentrations of said first substances and dimethyl sulfoxide are effective to stabilize the nucleic acids of said at least one cell in a specimen at ambient temperature, and further wherein the combined concentration of said first substances and dimethyl sulfoxide is 100% of said composition.

2. The composition of claim 1 wherein said first or second alcohol or ketone is selected from the group consisting of methanol, ethanol, propanol, isopropanol, butanol and acetone.

3. The composition of claim 1 wherein said concentrations of said first substances and dimethyl sulfoxide in said composition are in a ratio of 2.5:2.5:5 (first alcohol or ketone : second alcohol or ketone : dimethyl sulfoxide).

4. The composition of claim 1 wherein said concentrations of said first substances and dimethyl sulfoxide in said composition are in a ratio of 1:1 (first substance: dimethyl sulfoxide).

5. The composition of claim 3 wherein said first alcohol or ketone is methanol, said second alcohol or ketone is ethanol.

6. The composition of claim 4 wherein said first substance is methanol.

7. The composition of claim 1 wherein said nucleic acid is DNA.

8. The composition of claim 1 wherein said nucleic acid is RNA.

9. The composition of claim 8 wherein said RNA is ribosomal RNA.

10. The composition of claim 1 wherein said at least one cell is a prokaryote or eukaryote.

11. The composition of claim 1 wherein said at least one cell is a microorganism.

* * * * *